United States Patent [19]

Bratz et al.

[11] Patent Number: 5,605,875
[45] Date of Patent: Feb. 25, 1997

[54] HERBICIDAL COMPOSITIONS COMPRISING 3-(2-CHLOROPHENYLMETHYL)-1-(1-METHYL-1-PHENYLETHYL)- AND/OR 1-(METHYL-1-PHENYLETHYL)-3-(4-TOLYL)UREA AND AT LEAST ONE CYCLOHEXENONE OXIME ETHER

[75] Inventors: Matthias Bratz, Limburgerhof; Ulf Misslitz, Neustadt; Jürgen Kast, Böhl-Iggelheim; Wilhelm Rademacher, Limburgerhof; Helmut Walter, Obrigheim, all of Germany

[73] Assignee: BASF Aktiengesellschaft, Ludwigshafen, Germany

[21] Appl. No.: 458,041

[22] Filed: Jun. 1, 1995

[30] Foreign Application Priority Data

Jun. 3, 1994 [DE] Germany .................... 44 19 513.3

[51] Int. Cl.$^6$ .................................................. A01N 25/32
[52] U.S. Cl. ............................................ 504/100; 504/111
[58] Field of Search ...................................... 504/100, 111

[56] References Cited

U.S. PATENT DOCUMENTS

| | | | |
|---|---|---|---|
| 5,030,269 | 7/1991 | Barton et al. | 71/88 |
| 5,084,083 | 1/1992 | Lewis et al. | 71/90 |
| 5,280,007 | 1/1994 | Kawai | 504/105 |
| 5,362,704 | 11/1994 | Goto et al. | 504/134 |
| 5,401,700 | 3/1995 | Sohn et al. | 504/106 |

FOREIGN PATENT DOCUMENTS

| | | |
|---|---|---|
| 2072229 | 12/1992 | Canada . |
| 2078469 | 3/1993 | Canada . |
| 293062 | 11/1988 | European Pat. Off. . |
| 4209475 | 9/1993 | Germany . |
| 5/155710 | 12/1991 | Japan . |
| 5/155720 | 12/1991 | Japan . |
| 5/155721 | 12/1991 | Japan . |
| 5/255018 | 3/1992 | Japan . |

OTHER PUBLICATIONS

CA 119:111301u. Abstract of JP 5–97,614 Oct. 1, 1991.
CA 119:111307a Abstract of JP 5–117,118 Oct. 28, 1991.
CA 119:154020u Abstract of JP 5–139,920 Nov. 20, 1991.

*Primary Examiner*—S. Mark Clardy
*Attorney, Agent, or Firm*—Keil & Weinkauf

[57] ABSTRACT

Herbicidal compositions containing at least one liquid and/or solid carrier, if desired at least one adjuvant, and
a) an antagonistically active amount of 3-(2-chlorophenylmethyl)-1-(1-methyl-1-phenylethyl)urea and/or 1-(1-methyl-1-phenylethyl)-3-(4-tolyl)urea
and
b) a herbicidally active amount of at least one cyclohexenone oxime ether.

16 Claims, No Drawings

HERBICIDAL COMPOSITIONS COMPRISING 3-(2-CHLOROPHENYLMETHYL)-1-(1-METHYL-1-PHENYLETHYL)- AND/OR 1-(METHYL-1-PHENYLETHYL)-3-(4-TOLYL)UREA AND AT LEAST ONE CYCLOHEXENONE OXIME ETHER

The present invention relates to novel herbicidal compositions which contain at least one liquid and/or solid carrier, if desired at least one adjuvant, and an antagonistically active amount of a) 3-(2-chlorophenylmethyl)-1-(1-methyl-1-phenylethyl)urea and/or 1-(1-methyl-1-phenylethyl)-3-(4-tolyl)urea and b) a herbicidally active amount of at least one cyclohexenone oxime ether.

The invention additionally relates to processes for preparing these compositions and for the selective control of undesired plant growth on areas for cultivation of crop plants.

Herbicidally active cyclohexenone oxime ethers are, as a rule, highly suitable for controlling monocotyledon weeds in broad-leaved crops. Their tolerability by grass-like crop plants such as corn, rice, wheat, barley and millet, however, is not always entirely adequate, ie. in addition to the undesired plants the crop plants are also damaged to an intolerably high extent. A decrease in the application rate, which is in general desirable, has the disadvantage that although the crop plants are saved, at the same time, however, the undesirable plants are also only inadequately controlled.

A method of making possible the use of herbicidal cyclohexenone oxime ethers in cereal crops is to apply, in addition to the herbicides, a second component called a safener, antidote or antagonist, whereby the damage to the crop plants is decreased or completely avoided.

EP-A 537 463, EP-A 520 371, EP-A 333 131 and EP-A 293 062 disclose eg. heterocyclic compounds which act antagonistically with respect to the cyclohexenone oxime ethers. The effect on the crop plants, however, is not always completely satisfactory.

3-(2-Chlorophenylmethyl)-1-(1-methyl-1-phenylethyl)urea and 1-(1-methyl-1-phenylethyl)-3-(4-tolyl)urea have already been described as components in herbicidally active mixtures (cf. eg. DE-A 42 09 475, JP-A 05/097 614, JP-A 05/177 118, JP-A 05/155 710, JP-A 05/155 720, JP-A 05/155 721, JP-A 05/139 920, JP-A 05/255 018 and U.S. Pat. No. 5,280,007).

It is an object of the present invention to provide herbicidal compositions which guarantee good control of undesirable plants without, however, noticeably damaging the crop plants or significantly reducing their harvest yield.

We have found that this object is achieved by the herbicidal compositions defined at the beginning.

In addition, processes for preparing these compositions and for treating plant crops with the antagonistically active ureas and herbicidally active cyclohexenone oxime ethers have been found, it being insignificant whether the ureas and the cyclohexenone oxime ethers are formulated and applied together or separately and in what sequence the application takes place on separate application.

Beside the antagonistically and herbicidally active compounds, additionally other antagonistically or pesticidally active substances can be contained.

The herbicidally active cyclohexenone oxime ethers which contain the following essential structural feature

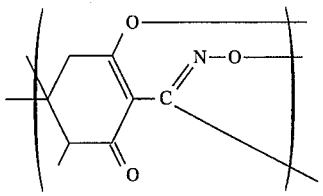

are disclosed, inter alia, in DE-A 24 39 104, DE-A 28 22 304, DE-A 38 08 072, DE-A 38 38 309, EP-A 046 860, EP-A 066 195, EP-A 071 707, EP-A 088 299, EP-A 088 301, EP-A 115 808, EP-A 125 094, EP-A 137 174, EP-A 142 741, EP-A 177 913, EP-A 228 598, EP-A 230 235, EP-A 230 260, EP-A 238 021, EP-A 243 313, EP-A 254 514, EP-A 319 835, EP-A 456 068, EP-A 456 069, EP-A 456 112, EP-A 456 118, U.S. Pat. No. 4,440,566, JP-A 54/191 945 and Proceedings Brit. Crop-Protection Conference—Weeds 1985, Vol. 1, pages 93–98.

Specifically, the herbicidal compositions contain as component b) a cyclohexenone oxime ether of the general formula I

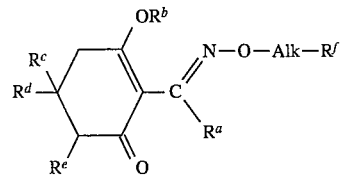

where the substituents have the following meanings:

$R^a$ is $C_1$–$C_6$-alkyl;

$R^b$ is hydrogen, an equivalent of an agriculturally utilizable cation, ($C_1$–$C_8$-alkyl)carbonyl, $C_1$–$C_{10}$-alkylsulfonyl, $C_1$–$C_{10}$-alkylphosphonyl, benzoyl, benzenesulfonyl or benzenephosphonyl, it being possible for the aromatic rings, if desired, to carry one to five halogen atoms;

$R^c$ is hydrogen, cyano, formyl or $C_1$–$C_6$-alkyl, which can carry one of the following radicals: $C_1$–$C_4$-alkoxy, $C_1$–$C_4$-alkylthio, phenoxy, phenylthio, pyridyloxy or pyridylthio, it being possible for the phenyl and pyridyl rings, if desired, in turn to carry one to three substituents selected from the group consisting of nitro, cyano, halogen, $C_1$–$C_4$-alkyl, $C_1$–$C_4$-haloalkyl, $C_1$–$C_4$-alkoxy, $C_1$–$C_4$-haloalkoxy, $C_1$–$C_4$-alkylthio, $C_3$–$C_6$-alkenyl, $C_3$–$C_6$-alkenyloxy, $C_3$–$C_6$-alkynyl, $C_3$–$C_6$-alkynyloxy and —$NR^gR^h$, where $R^g$ is hydrogen, $C_1$–$C_4$-alkyl, $C_3$–$C_6$-alkenyl, $C_3$–$C_6$-alkynyl, ($C_1$–$C_6$-alkyl)carbonyl or benzoyl, which, if desired, can carry one to three radicals selected from the group consisting of nitro, cyano, halogen, $C_1$–$C_4$-alkyl, $C_1$–$C_4$-haloalkyl, $C_1$–$C_4$-alkoxy and $C_1$–$C_4$-alkylthio, and $R^h$ is hydrogen, $C_1$–$C_4$-alkyl, $C_3$–$C_6$-alkenyl or $C_3$–$C_6$-alkynyl;

$C_3$–$C_7$-cycloalkyl or $C_5$–$C_7$-cycloalkenyl, it being possible for these cyclic systems, if desired, to carry one to three radicals selected from the group consisting of hydroxyl, halogen, $C_1$–$C_4$-alkyl, $C_1$–$C_4$-haloalkyl, $C_1$–$C_4$-alkoxy, $C_1$–$C_4$-alkylthio, benzylthio, $C_1$–$C_4$-alkylsulfonyl, $C_1$–$C_4$-alkylsulfenyl and $C_1$–$C_4$-alkylsulfinyl;

a 5-membered saturated heterocycle which, in addition to carbon atoms, contains one or two oxygen or sulfur atoms or an oxygen atom and a sulfur atom as ring members, and which if desired can carry one to three radicals selected from the group consisting of $C_1$–$C_4$-alkyl, $C_1$–$C_4$-haloalkyl, $C_1$–$C_4$-alkoxy and $C_1$–$C_4$-alkylthio;

a 6- or 7-membered saturated or mono- or diunsaturated heterocycle which, in addition to carbon atoms, contains one or two oxygen or sulfur atoms or one oxygen and one sulfur atom as ring members, and which if desired can carry one to three radicals selected from the group consisting of hydroxyl, halogen, $C_1$–$C_4$-alkyl, $C_1$–$C_4$-haloalkyl, $C_1$–$C_4$-alkoxy and $C_1$–$C_4$-alkylthio;

a 5-membered heteroaromatic system which, in addition to carbon atoms, contains one or two nitrogen atoms and one oxygen or sulfur atom or one to three nitrogen atoms or one oxygen or one sulfur atom as ring members and which, if desired, can carry one to three radicals selected from the group consisting of cyano, halogen, $C_1$–$C_4$-alkyl, $C_1$–$C_4$-haloalkyl, $C_1$–$C_4$-alkoxy, $C_1$–$C_4$-haloalkoxy, $C_1$–$C_4$-alkylthio, $C_2$–$C_6$-alkenyl, $C_2$–$C_6$-alkenyloxy, $C_2$–$C_6$-alkynyl, $C_2$–$C_6$-alkynyloxy and $C_1$–$C_4$-alkoxy-$C_1$–$C_4$-alkyl;

phenyl or pyridyl, which both, if desired, can carry one to three radicals selected from the group consisting of nitro, cyano, formyl, halogen, $C_1$–$C_4$-alkyl, $C_1$–$C_4$-haloalkyl, $C_1$–$C_4$-alkoxy, $C_1$–$C_4$-haloalkoxy, $C_1$–$C_4$-alkylthio, $C_2$–$C_6$-alkenyl, $C_2$–$C_6$-alkenyloxy, $C_3$–$C_6$-alkynyl, $C_3$–$C_6$-alkynyloxy and -$NR^gR^h$;

$R^d$ is hydrogen, hydroxyl or, if $R^c$ is $C_1$–$C_6$-alkyl, also $C_1$–$C_6$-alkyl;

$R^e$ is hydrogen, cyano, halogen, ($C_1$–$C_4$-alkoxy)carbonyl or ($C_1$–$C_4$-alkyl)ketoxime;

Alk is a $C_1$–$C_6$-alkylene, $C_3$–$C_6$-alkenylene or $C_3$–$C_6$-alkynylene chain which in each case can carry a methylene group (=$CH_2$) and/or one to three of the following radicals: halogen and/or $C_1$–$C_3$-alkyl;

a saturated or unsaturated 3- to 6-membered chain which, in addition to carbon members, contains one of the following bridge members: oxygen or sulfur, —SO—, —$SO_2$— or —N($R^i$)—, and which if desired can carry one to three $C_1$–$C_3$-alkyl and/or halogen substituents, $R^i$ being hydrogen, $C_1$–$C_4$-alkyl, $C_3$–$C_6$-alkenyl or $C_3$–$C_6$-alkynyl;

$R^f$ is hydrogen or —CH=CH—Z,

Z being hydrogen, cyano, carboxyl, halogen, $C_1$–$C_4$-alkyl, $C_1$–$C_4$-haloalkyl, $C_1$–$C_4$-alkoxy, ($C_1$–$C_8$-alkoxy)carbonyl, benzyloxycarbonyl or $C_3$–$C_6$-cycloalkyl which, if desired, can carry one to three radicals selected from the group consisting of hydroxyl, halogen, $C_1$–$C_4$-alkyl, $C_1$–$C_4$-haloalkyl and $C_1$–$C_4$-alkoxy, or is phenyl, halophenyl, dihalophenyl, thienyl or pyridyl, it being possible for these 5 rings, if desired, to carry one to three radicals selected from the group consisting of nitro, cyano, halogen, $C_1$–$C_4$-alkyl, $C_1$–$C_4$-haloalkyl, $C_1$–$C_4$-alkoxy, $C_1$–$C_4$-haloalkoxy, $C_1$–$C_4$-alkylthio and $C_3$–$C_6$-cycloalkyl, it being possible for the cyclic radical, if desired, in turn to carry one to three substituents selected from the group consisting of halogen, $C_1$–$C_4$-alkyl, $C_1$–$C_4$-haloalkyl and $C_1$–$C_4$-alkoxy;

ethynyl which can carry a $C_1$–$C_4$-alkyl or $C_3$–$C_6$-cycloalkyl radical, it being possible for these radicals, if desired, in turn to carry one to three substituents selected from the group consisting of hydroxyl, halogen, $C_1$–$C_4$-alkyl, $C_1$–$C_4$-haloalkyl and $C_1$–$C_4$-alkoxy;

ethynyl which carries a phenyl, thienyl or pyridyl radical, it being possible for the aromatic radicals, if desired, in turn to carry one to three substituents selected from the group consisting of nitro, cyano, halogen, $C_1$–$C_4$-alkyl, $C_1$–$C_4$-haloalkyl, $C_1$–$C_4$-alkoxy, $C_1$–$C_4$-haloalkoxy and $C_1$–$C_4$-alkylthio;

phenyl, phenoxy, a 5-membered heteroaromatic system which, in addition to carbon ring members, contains one or two nitrogen atoms and an oxygen or sulfur atom or one to three nitrogen atoms or an oxygen or a sulfur atom, or a 6-membered heteroaromatic system which, in addition to carbon ring members, contains one to four nitrogen atoms, it being possible for the phenyl ring and the heteroaromatic systems, if desired, to carry one to three radicals selected from the group consisting of nitro, $C_1$–$C_4$-alkoxy, $C_1$–$C_4$-haloalkoxy, $C_1$–$C_4$-alkylthio, $C_1$–$C_4$-haloalkylthio, a substituent Z and a substituent —$NR^kR^l$, $R^k$ being hydrogen, $C_1$–$C_4$-alkyl, $C_3$–$C_6$-alkenyl or $C_3$–$C_6$-alkynyl and $R^l$ being hydrogen, $C_1$–$C_4$-alkyl, $C_3$–$C_6$-alkenyl, $C_3$–$C_6$-alkynyl, ($C_1$–$C_6$-alkyl)carbonyl or benzoyl which, if desired, can carry one to three radicals selected from the group consisting of nitro, cyano, halogen, $C_1$–$C_4$-alkyl, $C_1$–$C_4$-haloalkyl, $C_1$–$C_4$-alkoxy and $C_1$–$C_4$-alkylthio.

Among the abovementioned cyclohexenone oxime ethers I, those compounds I are particularly preferred where Alk is a $C_1$–$C_4$-alkyl, $C_3$–$C_4$-alkenyl or $C_3$–$C_4$-alkynyl chain which in each case can carry one of the following substituents: halogen or $C_1$–$C_3$-alkyl and $R^f$ is phenyl which, if desired, can carry one to three substituents selected from the group consisting of nitro, cyano, halogen, $C_1$–$C_4$-alkyl, $C_1$–$C_4$-haloalkyl, phenyl, halophenyl and phenoxy, or phenoxy which, if desired, in turn can carry one to three substituents selected from a group consisting of nitro, cyano, halogen, $C_1$–$C_4$-alkyl and $C_1$–$C_4$-haloalkyl.

The following meanings of $R^c$, $R^e$, Alk and $R^f$ are very particularly preferred, namely per se or in combination:

$R^c$ is hydrogen, cyano, formyl or $C_1$–$C_6$-alkyl which can carry one of the following radicals: $C_1$–$C_4$-alkoxy, $C_1$–$C_4$-alkylthio, phenoxy or phenylthio, it being possible for the phenyl rings, if desired, in turn to carry one to three substituents selected from the group consisting of nitro, cyano, halogen, $C_1$–$C_4$-alkyl, $C_1$–$C_4$-haloalkyl, $C_1$–$C_4$-alkoxy, $C_1$–$C_4$-haloalkoxy and $C_1$–$C_4$-alkylthio;

$C_3$–$C_7$-cycloalkyl or $C_5$–$C_7$-cycloalkenyl, it being possible for these cyclic systems, if desired, to carry one to three radicals selected from the group consisting of hydroxyl, halogen, $C_1$–$C_4$-alkyl, $C_1$–$C_4$-haloalkyl, $C_1$–$C_4$-alkoxy, $C_1$–$C_4$-alkylthio, benzylthio, $C_1$–$C_4$-alkylsulfonyl, $C_1$–$C_4$-alkylsulfenyl and $C_1$–$C_4$-alkylsulfinyl;

a 6- or 7-membered saturated or mono- or diunsaturated heterocycle which, in addition to carbon atoms, contains one or two oxygen or sulfur atoms or one oxygen and one sulfur atom as ring members and which, if desired, can carry one to three radicals selected from the group consisting of hydroxyl, halogen, $C_1$–$C_4$-alkyl, $C_1$–$C_4$-haloalkyl, $C_1$–$C_4$-alkoxy and $C_1$–$C_4$-alkylthio;

a 5-membered heteroaromatic system which, in addition to carbon atoms, contains one or two nitrogen atoms and one oxygen or sulfur atom or one to three nitrogen atoms or one oxygen or one sulfur atom as ring members, and which, if desired, can carry one to three radicals selected from the group consisting of cyano, halogen, $C_1$–$C_4$-alkyl, $C_1$–$C_4$-haloalkyl, $C_1$–$C_4$-alkoxy, $C_1$–$C_4$-haloalkoxy, $C_1$–$C_4$-alkylthio and $C_1$–$C_4$-alkoxy-$C_1$–$C_4$-alkyl;

phenyl or pyridyl which both, if desired, can carry one to three radicals selected from the group consisting of nitro, cyano, formyl, halogen, $C_1$–$C_4$-alkyl, $C_1$–$C_4$-haloalkyl, $C_1$–$C_4$-alkoxy, $C_1$–$C_4$-haloalkoxy and $C_1$–$C_4$-alkylthio;

$R^e$ is hydrogen;

Alk is a $C_1$–$C_6$-alkylene, $C_3$–$C_6$-alkenylene or $C_3$–$C_6$-alkynylene chain which can in each case carry a methylene group (=$CH_2$) and/or one to three of the following radicals: halogen and/or $C_1$–$C_3$-alkyl;

a saturated or unsaturated 3- to 6-membered chain which, in addition to carbon members, contains one of the following bridge members: oxygen or sulfur, —SO—, —$SO_2$— or —N($R^i$)—, and which, if desired, can carry one to three $C_1$–$C_3$-alkyl and/or halogen substituents;

$R^f$ is hydrogen, —CH=CH—Z,

Z being hydrogen, cyano, carboxyl, halogen, $C_1$–$C_4$-alkyl, $C_1$–$C_4$-haloalkyl, $C_1$–$C_4$-alkoxy, ($C_1$–$C_8$-alkoxy)carbonyl, benzyloxycarbonyl, $C_3$–$C_6$-cycloalkyl which, if desired, can carry one to three radicals selected from the group consisting of hydroxyl, halogen, $C_1$–$C_4$-alkyl, $C_1$–$C_4$-haloalkyl and $C_1$–$C_4$-alkoxy, or is phenyl, halophenyl, dihalophenyl, thienyl or pyridyl, it being possible for these 5 rings, if desired, to carry one to three radicals selected from the group consisting of nitro, cyano, halogen, $C_1$–$C_4$-alkyl, $C_1$–$C_4$-haloalkyl, $C_1$–$C_4$-alkoxy, $C_1$–$C_4$-haloalkoxy, $C_1$–$C_4$-alkylthio and $C_3$–$C_6$-cycloalkyl which, if desired, in turn can additionally carry one to three substituents selected from the group consisting of halogen, $C_1$–$C_4$-alkyl, $C_1$–$C_4$-haloalkyl and $C_1$–$C_4$-alkoxy;

or phenyl which, if desired, can carry one to three radicals selected from the group consisting of nitro, cyano, halogen, $C_1$–$C_4$-alkyl, $C_1$–$C_4$-haloalkyl, phenyl, halophenyl and phenoxy which, if desired, in turn can carry one to three substituents selected from the group consisting of halogen, $C_1$–$C_4$-alkyl and $C_1$–$C_4$-haloalkyl.

Those cyclohexenone oxime ethers of the formula I have hitherto proven particularly advantageous where the substituents have the following meanings:

$R^a$ is ethyl or propyl;

$R^b$ is hydrogen or an equivalent of an agriculturally utilizable cation;

$R^c$ is 2-(ethylthio)propyl, tetrahydrothiopyran-3-yl, tetrahydro-thiopyran-4-yl, tetrahydropyran-3-yl, tetrahydropyran-4-yl, 1-(methylthio)cyclopropyl, 5-(isopropyl)isoxazol-3-yl, 2,5-dimethylpyrazol-3-yl, 2,4,6-trimethylphenyl or 2-phenylthioethyl which, if desired, can carry one or two cyano, fluorine, chlorine and/or methyl substituents on the phenyl ring;

$R^d$ and $R^e$ are hydrogen;

Alk is a chain —$CH_2$—$CH_2$—, —$CH_2$—CH($CH_3$)—, —$CH_2$—CH=CH—, —$CH_2$—CH=C(Cl)— or —$CH_2$—$CH_2$—CH=CH— and $R^f$ is hydrogen, phenyl, halophenyl, dihalophenyl, phenoxy, halophenoxy or dihalophenoxy.

The following cyclohexenone oxime ethers I are very particularly preferred as component b):

2-(N-ethoxybutyrimidoyl)-5-(2-ethylthiopropyl)-3-hydroxy-2-cyclohexen-1-one, 2-(1-allyloxyiminobutyl)-4-methoxycarbonyl-5,5-dimethyl-3-oxocyclohexenol, 2-(N-ethoxybutyrimidoyl)-5-(2-phenylthiopropyl)-3-hydroxy-2-cyclohexen-1-one, 5-(2,4,6-trimethylphenyl)-3-hydroxy-2-[1-(ethoxyimino)propyl]cyclohex-2-en-1-one, 2-(N-ethoxybutyrimidoyl)-3-hydroxy-5-(tetrahydropyran-3-yl)-cyclohexen-1-one, 1-[1-(ethoxyimino)butyl]-3-hydroxy-5-(tetrahydrothiopyran-3-yl)-2-cyclohexen-1-one, 2-[1-[(E)-3-chloroallyloxy]iminopropyl]-5-(2-ethylthiopropyl)-3-hydroxycyclohex-2-enone, 2-(1-(3-chloroallyloxy)iminopropyl)-5-(2-ethylthio)propyl)-3-hydroxycyclohex-2-enone or 2-(1-(3-chloroallyloxy)iminopropyl)-5-(1,3-dimethylpyrazol-5-yl-3-hydroxycyclohex-2-enone.

Both the pure enantiomers and the racemates or diastereomer mixtures of the cyclohexenone oxime ethers I are suitable as herbicidal active compounds.

Herbicidal active compounds and compounds having antagonistic activity can be applied to the leaves and shoots together or separately after emergence of the plants. Preferably, in this case, 3-(2-chlorophenylmethyl)-1-(1-methyl-1-phenylethyl)urea and/or 1-(1-methyl-1-phenylethyl)-3-(4-tolyl)urea is applied simultaneously with the herbicidal active compound. However, it is also possible to apply antidote and herbicidal active compound separately.

There is furthermore the possibility of treating the seeds or seedlings of the crop plants, before sowing them or transplanting, with 3-(2-chlorophenylmethyl)-1-(1-methyl-1-phenylethyl)urea and/or 1-(1-methyl-1-phenylethyl)-3-(4-tolyl)urea, in this case the herbicidal active compound then being applied on its own in the customary manner.

In the ready-to-use preparation, herbicide and antagonist can be present together or separately formulated in suspended, emulsified or dissolved form. The application forms depend completely here on the intended uses.

The compositions according to the invention or, in the case of separate application the herbidical active compounds or the antidote, are applied by spraying, atomizing, dusting, broadcasting or watering, for example in the form of directly sprayable solutions, powders, suspensions, even high-percentage aqueous, oily or other suspensions, or dispersions, emulsions, oil dispersions, pastes, dusting compositions, broadcasting compositions or granules.

To prepare directly sprayable solutions, emulsions, pastes and oil dispersions, petroleum fractions of medium to high boiling point, eg. kerosene or diesel oil, and also coal tar oils, and oils of vegetable or animal origin, aliphatic, cyclic or aromatic hydrocarbons, eg. benzene, toluene, xylene, paraffin, tetrahydronaphthalene, alkylated naphthalenes or their derivatives, alcohols such as methanol, ethanol, propanol, butanol and cyclohexanol, chlorohydrocarbons such as chloroform, carbon tetrachloride and chlorobenzene, ketones such as cyclohexanone and isophorone, strongly polar solvents, eg. dimethylformamide, dimethyl sulfoxide, N-methylpyrrolidone and water are customarily suitable.

Aqueous application forms can be prepared from emulsion concentrates, pastes or wettable powders, or oil dispersions by addition of water. To prepare emulsions, pastes or oil dispersions, herbicidal active compound and/or antidote can be homogenized in water, as such or dissolved in an oil or solvent, by means of wetting agents, adherents, dispersants or emulsifiers. However, concentrates consisting of herbicidal active compound and/or antidote, wetting agent, adherent, dispersant and emulsifier and possibly solvent or oil can also be prepared, which are suitable for dilution with water.

Suitable surface-active substances are alkali metal, alkaline earth metal or ammonium salts of lignosulfonic acid, naphthalenesulfonic acid, phenolsulfonic acid, alkylarylsulfonates, alkylsulfates, alkylsulfonates, alkali metal and alkaline earth metal salts of dibutylnaphthalenesulfonic acid, lauryl ether sulfate, fatty alcohol sulfates, fatty acid alkali metal and alkaline earth metal salts, salts of sulfated hexadecanols, heptadecanols or octadecanols, salts of sulfated fatty alcohol glycol ethers, condensation products of sulfonated naphthalene and naphthalene derivatives with formaldehyde, condensation products of naphthalene or of naphthalenesulfonic acids with phenol and formaldehyde, polyoxyethylene octylphenyl ether, ethoxylated isooctylphenol, octylphenol, nonylphenol, alkylphenyl polyglycol ethers, tributylphenyl polyglycol ethers, alkylaryl polyether alcohols, isotridecyl alcohol, fatty alcohol-ethylene oxide condensates, ethoxylated castor oil, polyoxyethylene or polyoxypropylene alkyl ethers, lauryl alcohol polyglycol ether acetal, sorbitol esters, lignin-sulfite waste liquors and methylcellulose.

Powder, broadcasting and dusting compositions can be prepared by mixing or joint grinding of herbicidal active compound and/or antidote with a solid carrier.

Granules, eg. coated, impregnated and homogeneous granules, can be prepared by binding of the active compounds to solid carriers. Suitable carriers are eg. mineral earths such as silicic acids, silica gels, silicates, talc, kaolin, attapulgite, limestone, chalk, bole, loess, clay, dolomite, diatomaceous earth, calcium sulfate and magnesium sulfate, magnesium oxide, ground synthetic materials, fertilizers such as ammonium sulfate, ammonium phosphate, ammonium nitrate and ureas, vegetable products such as cereal meals, tree bark meal, wood meal and nutshell meal and also cellulose powder.

Formulations contain from 0.1 to 95% by weight of component a) {antidote} and b) {cyclohexenone oxime ether}, preferably from 0.5 to 90% by weight.

In the case of application of the antidote to seed or in the case of treatment of seedlings, solutions are preferably employed which contain at least one antagonistic active compound in a concentration of from 1 to 100,000 ppm, in particular 100 to 10,000 ppm.

The application rates of cyclohexenone oxime ether(s) are from 0.005 to 2 kg/ha. Depending on the particular crop plant and the herbicide used, different amounts of antagonist are needed. Suitable quantitative ratios of component a) {antagonist} to component b) {cyclohexenone oxime ether} are from 1:10 to 1:0.01, preferably from 1:4 to 1:0.1, parts by weight.

In the case of seed treatment, in general amounts of active compound of from 0.01 to 10 g, preferably from 0.1 to 2 g, per kilogram of seed are needed.

In addition to 3-(2-chlorophenylmethyl)-1-(1-methyl-1-phenylethyl)urea and/or 1-(1-methyl-1-phenylethyl)-3-(4-tolyl)urea and at least one cyclohexenone oxime ether I, the novel herbicidal compositions can contain further herbicidal or growth-regulating active compounds of different chemical structure.

EXAMPLE OF THE BIOLOGICAL ACTION

The effect of various representatives of the herbicidal compositions or composition combinations according to the invention, consisting of 3-(2-chlorophenylmethyl)-1-(1-methyl-1-phenylethyl) urea (common name: cumyluron, dibenzyluron) or 1-(1-methyl-1-phenylethyl)-3-(4-tolyl)urea (common name: dymron) and herbicide, on the growth of undesirable plants and crop plants in comparison with the herbicidal active compound on its own is confirmed by the following biological examples from greenhouse tests:

In the greenhouse tests, the cultivation containers used were plastic flowerpots containing around 300 cm$^3$ of loamy sand with about 3.0% by weight of humus as a substrate. The seeds of the test plants were evenly sown according to species and moistened. The containers were then covered with transparent plastic hoods until the seeds had germinated uniformly, and the seedlings were raised.

List of the Test Plants

| Botanical name | Common name |
| --- | --- |
| Zea mays | corn, maize |
| Triticum aestivum | wheat (Star variety) |
| Avena fatua | wild oat |
| Setaria viridis | green foxtail (green bristle-grass) |

For postemergence treatment, the test plants were each raised to a height of growth of from 3 to 20 cm, depending on growth form, and only then treated. The herbicidal cyclohexenone oxime ethers were in this case suspended or emulsified in water as a dispersing agent and sprayed by means of finely dispersing nozzles.

In the preemergence process, in a similar manner active compound preparations were sprayed onto the soil surface immediately after sowing.

The exemplary herbicide used was

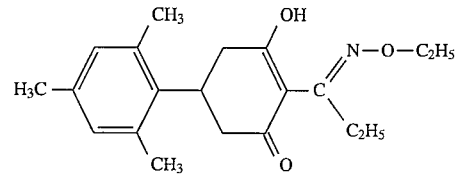

Common name: tralkoxydim

The two antagonistically active compounds were prepared for postemergence treatment in a mixture consisting of 80% by weight of cyclohexenone as diluent and 20% by weight of surfactant (Emulphor EL $^1$) with 10% by weight of active compound.

$^1$ 8-times ethoxylated castor oil.

For comparison, the herbicidal cyclohexenone oxime ether was formulated as a 10 to 20% strength by weight emulsion concentrate and in each case employed with the addition of that amount of solvent system to the spray mixture in which the compound having antagonistic activity was applied. The solution was prepared by mixing the active compound into a solution of 93% by weight of xylene and 7% by weight of Lutensol®AP-8 $^2$.

$^2$ nonionic surface-active agent based on alkylphenyl polyethylene glycol ethers.

After application of the respective active compound mixture by means of finely dispersing nozzles, the test plants were cultivated in a greenhouse, to be specific heat-loving species at from about 18° to 30° C. and those from more moderate climates at from about 10° to 25° C.

The test period extended over 3 to 5 weeks, during which the plants were tended. Their reaction to the active compound treatment was then recorded. Assessment was carried out in comparison with the untreated control plants using a scale of from 0 to 100, 0 meaning no damage and 100 complete destruction of at least the above-ground parts of the plants.

The improvement in the tolerability of herbicidally active cyclohexenone oxime ethers by crop plants from the Gramineae family (grasses) such as wheat and corn by cumyluron or dymron can be seen from Tables 1 and 2 which follow:

TABLE 1

Improvement in the tolerability of the herbicide tralkoxydim by wheat by admixing cumyluron during postemergence application in a greenhouse:

| Application rate [kg/ha] | | Test plants and damage [%] | | |
|---|---|---|---|---|
| | | Crop plant | undesirable plants | |
| | | | | Avena |
| Antidote | Herbicide | wheat | Setaria viridis | fatua |
| — | 0.125 | 55 | 98 | 100 |
| 0.500 | 0.125 | 0 | 95 | 98 |
| 0.250 | 0.125 | 25 | 100 | 100 |
| 0.125 | 0.125 | 30 | 98 | 100 |

TABLE 2

Improvement in the tolerability of the herbicide tralkoxydim by wheat by admixing dymron during postemergence application in a greenhouse:

| Application rate [kg/ha] | | Test plants and damage [%] | | |
|---|---|---|---|---|
| | | Crop plant | undesirable plants | |
| | | | | Avena |
| Antidote | Herbicide | wheat | Setaria viridis | fatua |
| — | 0.062 | 65 | 90 | 100 |
| 0.500 | 0.062 | 10 | 95 | 100 |
| 0.250 | 0.062 | 30 | 100 | 100 |
| 0.125 | 0.062 | 20 | 90 | 100 |

We claim:
1. A herbicidal composition which comprises: at least one liquid and/or solid carrier, and
  a) an antagonistically active amount of 3-(2-chlorophenyl-methyl-1-(1-methyl-1-phenylethyl)urea and/or 1-(1-methyl-1-phenylethyl)-3-(4-tolyl)urea and
  b) a herbicidally active amount of at least one cyclohexenone oxime ether of the formula I

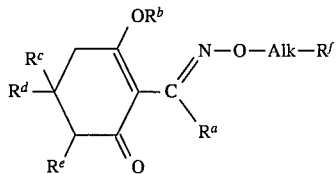

where the substituents have the following meanings:
$R^a$ is $C_1-C_6$-alkyl;
$R^b$ is hydrogen, an equivalent of an agriculturally utilizable cation, ($C_1-C_8$-alkyl)carbonyl, $C_1-C_{10}$-alkylsulfonyl, $C_1-C_{10}$-alkylphosphonyl, benzoyl, benzenesulfonyl or benzenephosphonyl, it being possible for the aromatic rings, if desired, to carry one to five halogen atoms;
$R^c$ is hydrogen, cyano, formyl or $C_1-C_6$-alkyl, which can carry one of the following radicals: $C_1-C_4$-alkoxy, $C_1-C_4$-alkylthio, phenoxy, phenylthio, pyridyloxy or pyridylthio, it being possible for the phenyl and pyridyl rings, if desired, in turn to carry one to three substituents selected from the group consisting of nitro, cyano, halogen, $C_1-C_4$-alkyl, $C_1-C_4$-haloalkyl, $C_1-C_4$-alkoxy, $C_1-C_4$-haloalkoxy, $C_1-C_4$-alkylthio, $C_3-C_6$-alkenyl, $C_3-C_6$-alkenyloxy, $C_3-C_6$-alkynyl, $C_3-C_6$-alkynyloxy and $—NR^gR^h$, where $R^g$ is hydrogen, $C_1-C_4$-alkyl, $C_3-C_6$-alkenyl, $C_3-C_6$-alkynyl, ($C_1-C_6$-alkyl) carbonyl or benzoyl, which, if desired, can carry one to three radicals selected from the group consisting of nitro, cyano, halogen, $C_1-C_4$-alkyl, $C_1-C_4$-haloalkyl, $C_1-C_4$-alkoxy and $C_1-C_4$-alkylthio,
and
$R^h$ is hydrogen, $C_1-C_4$-alkyl, $C_3-C_6$-alkenyl or $C_3-C_6$-alkynyl;
$C_3-C_7$-cycloalkyl or $C_5-C_7$-cycloalkenyl, it being possible for these cyclic systems, if desired, to carry one to three radicals selected from the group consisting of hydroxyl, halogen, $C_1-C_4$-alkyl, $C_1-C_4$-haloalkyl, $C_1-C_4$-alkoxy, $C_1-C_4$-alkylthio, benzylthio, $C_1-C_4$-alkylsulfonyl, $C_1-C_4$-alkylsulfenyl and $C_1-C_4$-alkylsulfinyl;
a 5-membered saturated heterocycle which, in addition to carbon atoms, contains one or two oxygen or sulfur atoms or an oxygen atom and a sulfur atom as ring members, and which if desired can carry one to three radicals selected from the group consisting of $C_1-C_4$-alkyl, $C_1-C_4$-haloalkyl, $C_1-C_4$-alkoxy and $C_1-C_4$-alkylthio;
a 6- or 7-membered saturated or mono- or diunsaturated heterocycle which, in addition to carbon atoms, contains one or two oxygen or sulfur atoms or one oxygen and one sulfur atom as ring members, and which if desired can carry one to three radicals selected from the group consisting of hydroxyl, halogen, $C_1-C_4$-alkyl, $C_1-C_4$-haloalkyl, $C_1-C_4$-alkoxy and $C_1-C_4$-alkylthio;
a 5-membered heteroaromatic system which, in addition to carbon atoms, contains one or two nitrogen atoms and one oxygen or sulfur atom or one to three nitrogen atoms or one oxygen or one sulfur atom as ring members and which, if desired, can carry one to three radicals selected from the group consisting of cyano, halogen, $C_1-C_4$-alkyl, $C_1-C_4$-haloalkyl, $C_1-C_4$-alkoxy, $C_1-C_4$-haloalkoxy, $C_1-C_4$-alkylthio, $C_2-C_6$-alkenyl, $C_2-C_6$-alkenyloxy, $C_2-C_6$-alkynyl, $C_2-C_6$-alkynyloxy and $C_1-C_4$-alkoxy-$C_1-C_4$-alkyl;
phenyl or pyridyl, which both, if desired, can carry one to three radicals selected from the group consisting of nitro, cyano, formyl, halogen, $C_1-C_4$-alkyl, $C_1-C_4$-haloalkyl, $C_1-C_4$-alkoxy, $C_1-C_4$-haloalkoxy, $C_1-C_4$-alkylthio, $C_2-C_6$-alkenyl, $C_2-C_6$-alkenyloxy, $C_3-C_6$-alkynyl, $C_3-C_6$-alkynyloxy and $—NR^gR^h$;
$R^d$ is hydrogen, hydroxyl or, if $R^c$ is $C_2-C_6$-alkyl, also $C_2-C_6$-alkyl;
$R^e$ is hydrogen, cyano, halogen, ($C_1-C_4$-alkoxy)carbonyl or ($C_1-C_4$-alkyl)ketoxime;
Alk is a $C_1-C_6$-alkylene, $C_3-C_6$-alkenylene or $C_3-C_6$-alkynylene chain which in each case can carry a methylene group ($=CH_2$) and/or one to three of the following radicals: halogen and/or $C_1-C_3$-alkyl;
a saturated or unsaturated 3- to 6-membered chain which, in addition to carbon members, contains one of the following bridge members: oxygen or sulfur, $—SO—$, $—SO_2—$ or $—N(R^i)—$, and which if desired can carry one to three $C_1-C_3$-alkyl and/or halogen substituents, $R^i$ being hydrogen, $C_1-C_4$-alkyl, $C_3-C_6$-alkenyl or $C_3-C_6$-alkynyl;
$R^f$ is hydrogen or $—CH=CH—Z$,
Z being hydrogen, cyano, carboxyl, halogen, $C_1-C_4$-alkyl, $C_1-C_4$-haloalkyl, $C_1-C_4$-alkoxy, ($C_1-C_8$-alkoxy- )carbonyl, benzyloxycarbonyl or $C_3$–$C_6$-cycloalkyl which, if desired, can carry one to three radicals selected from the group consisting of hydrolxyl, halogen, $C_1$–$C_4$-alkyl, $C_1$–$C_4$-haloalkyl and $C_1$–$C_4$-alkoxy, or is phenyl, halophenyl, dihalophenyl, thienyl or pyridyl, it being possible for these 5 rings, if desired, to carry one to three radicals selected from the group consisting of nitro, cyano, halogen, $C_1$–$C_4$-alkyl, $C_1$–$C_4$-haloalkyl, $C_1$–$C_4$-alkoxy, $C_1$–$C_4$-haloalkoxy, $C_1$–$C_4$-alkylthio and $C_3$–$C_6$-cycloalkyl, it being possible for the cyclic radical, if desired, in turn to carry one to three substituents selected from the group consisting of halogen, $C_1$–$C_4$-alkyl, $C_1$–$C_4$-haloalkyl and $C_1$–$C_4$-alkoxy;

ethynyl which can carry a $C_1$–$C_4$-alkyl or $C_3$–$C_6$-cycloalkyl radical, it being possible for these radicals, if desired, in turn to carry one to three substituents selected from the group consisting of hydroxyl, halogen, $C_1$–$C_4$-alkyl, $C_1$–$C_4$-haloalkyl and $C_1$–$C_4$-alkoxy;

ethynyl which carries a phenyl, thienyl or pyridyl radical, it being possible for the aromatic radical, if desired, in turn to carry one to three substituents selected from the group consisting of nitro, cyano, halogen, $C_1$–$C_4$-alkyl, $C_1$–$C_4$-haloalkyl, $C_1$–$C_4$-alkoxy, $C_1$–$C_4$-haloalkoxy and $C_1$–$C_4$-alkylthio;

phenyl, phenoxy, a 5-membered heteroaromatic system which, in addition to carbon ring members, contains one or two nitrogen atoms and an oxygen or sulfur atom or one to three nitrogen atoms or an oxygen or a sulfur atom, or a 6-membered heteroaromatic system which, in addition to carbon ring members, contains one to four nitrogen atoms it being possible for the phenyl ring and the heretoaromatic systems, if desired, to carry one to three radicals selected from the group consisting of nitro, $C_1$–$C_4$-alkoxy, $C_1$–$C_4$-haloalkoxy, $C_1$–$C_4$-alkylthio, $C_1$–$C_4$-haloalkylthio, a substituent Z and a substituent —$NR^kR^l$, $R^k$ being hydrogen, $C_1$–$C_4$-alkyl, $C_3$–$C_6$-alkenyl or $C_3$–$C_6$-alkynyl and $R^l$ being hydrogen, $C_1$–$C_4$-alkyl, $C_3$–$C_6$-alkenyl, $C_3$–$C_6$-alkynyl, ($C_1$–$C_6$-alkyl)carbonyl or benzoyl which, if desired, can carry one to three radicals selected from the group consisting of nitro, cyano, halogen, $C_1$–$C_4$-alkyl, $C_1$–$C_4$-haloalkyl, $C_1$–$C_4$-alkoxy and $C_1$–$C_4$-alkylthio.

2. A herbicidal composition as defined claimed in claim 1, where $R^c$ is hydrogen, cyano, formyl or $C_1$–$C_6$alkyl which can carry one of the following radicals: $C_1$–$C_4$-alkoxy, $C_1$–$C_4$-alkylthio, phenoxy or phenylthio, it being possible for the phenyl rings, if desired, in turn to carry one to three substituents selected from the group consisting of nitro, cyano, halogen, $C_1$–$C_4$-alkyl, $C_1$–$C_4$-haloalkyl, $C_1$–$C_4$-alkoxy, $C_1$–$C_4$-haloalkoxy and $C_1$–$C_4$-alkylthio;

$C_3$–$C_7$-cycloalkyl or $C_5$–$C_7$-cycloalkenyl, it being possible for these cyclic systems, if desired, to carry one to three radicals selected from the group consisting of hydroxyl, halogen, $C_1$–$C_4$-alkyl, $C_1$–$C_4$-haloalkyl, $C_1$–$C_4$-alkoxy, $C_1$–$C_4$-alkylthio, benzylthio, $C_1$–$C_4$-alkylsulfonyl, $C_1$–$C_4$-alkylsulfenyl and $C_1$–$C_4$-alkylsulfinyl;

a 6- or 7-membered saturated or mono- or diunsaturated heterocycle which, in addition to carbon atoms, contains one or two oxygen or sulfur atoms or one oxygen and one sulfur atom as ring members and which, if desired, can carry one to three radicals selected from the group consisting of hydroxyl, halogen, $C_1$–$C_4$-alkyl, $C_1$–$C_4$-haloalkyl, $C_1$–$C_4$-alkoxy and $C_1$–$C_4$-alkylthio;

a 5-membered heteroaromatic system which, in addition to carbon atoms, contains one or two nitrogen atoms and one oxygen or sulfur atom or one to three nitrogen atoms or one oxygen or one sulfur atom as ring members, and which, if desired, can carry one to three radicals selected from the group consisting of cyano, halogen, $C_1$–$C_4$-alkyl, $C_1$–$C_4$-haloalkyl, $C_1$–$C_4$-alkoxy, $C_1$–$C_4$-haloalkoxy, $C_1$–$C_4$-alkylthio and $C_1$–$C_4$-alkoxy-$C_1$–$C_4$-alkyl;

phenyl or pyridyl which both, if desired, can carry one to three radicals selected from the group consisting of nitro, cyano, formyl, halogen, $C_1$–$C_4$-alkyl, $C_1$–$C_4$-haloalkyl, $C_1$–$C_4$-alkoxY, $C_1$–$C_4$-haloalkoxy and $C_1$–$C_4$-alkylthio;

$R^e$ is hydrogen;

Alk is a $C_1$–$C_6$-alkylene, $C_3$–$C_6$-alkenylene or $C_3$–$C_6$-alkynylene chain which can in each case carry a methylene group (=$CH_2$) and/or one to three of the following radicals: halogen and/or $C_1$–$C_3$-alkyl;

a saturated or unsaturated 3- to 6-membered chain which, in addition to carbon members, contains one of the following bridge members: oxygen or sulfur, —SO—, —$SO_2$— or —N($R^i$)—, and which, if desired, can carry one to three $C_1$–$C_3$-alkyl and/or halogen substituents, $R^i$ being hydrogen, $C_1$–$C_4$-alkyl, $C_3$–$C_6$-alkenyl or $C_3$–$C_6$-alkynyl;

$R^f$ is hydrogen, —CH=CH—Z,

Z being hydrogen, cyano, carboxyl, halogen, $C_1$–$C_4$-alkyl, $C_1$–$C_4$-haloalkyl, $C_1$–$C_4$-alkoxy, ($C_1$–$C_8$-alkoxy)carbonyl, benzyloxycarbonyl, $C_3$–$C_6$-cycloalkyl which, if desired, can carry one to three radicals selected from the group consisting of hydroxyl, halogen, $C_1$–$C_4$-alkyl, $C_1$–$C_4$-haloalkyl and $C_1$–$C_4$-alkoxy, or is phenyl, halophenyl, dihalophenyl, thienyl or pyridyl, it being possible for these 5 rings, if desired, to carry one to three radicals selected from the group consisting of nitro, cyano, halogen, $C_1$–$C_4$-alkyl, $C_1$–$C_4$-haloalkyl, $C_1$–$C_4$-alkoxy $C_1$–$C_4$-haloalkoxy, $C_1$–$C_4$-alkylthio and $C_3$–$C_6$-cycloalkyl which, if desired, in turn can additionally carry one to three substituents selected from the group consisting of halogen, $C_1$–$C_4$-alkyl, $C_1$–$C_4$-haloalkyl and $C_1$–$C_4$-alkoxy;

or phenyl which, if desired, can carry one to three radicals selected from the group consisting of nitro, cyano, halogen, $C_1$–$C_4$-alkyl, $C_1$–$C_4$-haloalkyl, phenyl, halophenyl and phenoxy which, if desired, in turn can carry one to three substituents selected from the group consisting of halogen, $C_1$–$C_4$-alkyl and $C_1$–$C_4$-haloalkyl.

3. A herbicidal composition as defined in claim 1, where

Alk is a $C_1$–$C_4$-alkyl, $C_3$–$C_4$-alkenyl or $C_3$–$C_4$-alkynyl chain which in each case can carry one of the following substituents: halogen or $C_1$–$C_3$-alkyl and $R^f$ is phenyl which, if desired, can carry one to three substituents selected from the group consisting of nitro, cyano, halogen, $C_1$–$C_4$-alkyl, $C_1$–$C_4$-haloalkyl, phenyl, halophenyl and phenoxy, or phenoxy which, if desired, in turn can carry one to three substituents selected from a group consisting of nitro, cyano, halogen, $C_1$–$C_4$-alkyl and $C_1$–$C_4$-haloalkyl.

4. A herbicidal composition as defined in claim 1, where $R^a$ is ethyl or propyl;

$R^b$ is hydrogen or an equivalent of an agriculturally utilizable cation;

$R^c$ is 2-(ethylthio)propyl, tetrahydrothiopyran-3-yl, tetrahydrothiopyran-4-yl, tetrahydropyran-3-yl, tetrahydropyran-4-yl, 1-(methylthio)cyclopropyl, 5-(isopropyl) isoxazol-3-yl, 2,5-dimethylpyrazol-3-yl, 2,4,6-trimethylphenyl or 2-(phenylthio)ethyl which, if desired, can carry one or two cyano, fluorine, chlorine and/or methyl substituents on the phenyl ring;

$R^d$ and $R^e$ are hydrogen;

Alk is a chain —CH$_2$—CH$_2$—, —CH$_2$—CH(CH$_3$)—, —CH$_2$—CH=CH—, —CH$_2$—CH=C(Cl)— or —CH$_2$—CH$_2$—CH=CH— and $R^f$ is hydrogen, phenyl, halophenyl, dihalophenyl, phenoxy, halophenoxy or dihalophenoxy.

5. A herbicidal composition as defined in claim 1, comprising at least one of the following cyclohexenone oxime ethers I:

2-(N-ethoxybutyrimidoyl)-5-(2-ethylthiopropyl)-3-hydroxy-2-cyclohexen-1-one, 2-(1-allyloxyiminobutyl)-4-methoxycarbonyl-5,5-dimethyl-3-oxocyclohexenol, 2-(N-ethoxybutyrimidoyl)-5-(2-phenylthiopropyl)-3-hydroxy-2-cyclohexen-1-one, 5-(2,4,6-trimethylphenyl)-3-hydroxy-2-[1-(ethoxyimino)-propyl]cyclohex-2-en-1-one, 2-(N-ethoxybutyrimidoyl)-3-hydroxy-5-(tetrahydropyran-3-yl)-cyclohexen-1-one, 1-[1-(ethoxyimino)butyl]-3-hydroxy-5-(tetrahydrothiopyran-3-yl)-2-cyclohexen-1-one, 2-[1-[(E)-3-chloroallyloxy]iminopropyl]-5-(2-ethylthiopropyl)-3-hydroxycyclohex-2-enone, 2-(1-(3-chloroallyloxy)iminopropyl)-5-(2-ethylthio)-propyl)-3-hydroxycyclohex-2-enone or 2-(1-(3-chloroallyloxy)iminopropyl)-5-(1,3-dimethylpyrazol-5-yl-3-hydroxycyclohex-2-enone.

6. A herbicidal composition as defined in claim 1, wherein b is tralkoxydim.

7. A herbicidal composition as defined in claim 1, comprising a) 3-(2-chlorophenylmethyl)-1-(1-methyl-1-phenylethyl)urea and/or 1-(1-methyl-1-phenylethyl)-3-(4-tolyl)urea and b) at least one cyclohexenone oxime ether of the formula I in the weight ratio a):b) of from 0.01:1 to 10:1.

8. A herbicidal composition as defined in claim 7, wherein b is tralkoxydim.

9. A method of controlling undesirable plant growth, which comprises simultaneously or successively applying a) an antagonistically active amount of 3-(2-chlorophenylmethyl)-1-(1-methyl-1-phenylethyl)urea and/or 1-(1-methyl-1-phenylethyl)-3-(4-tolyl)urea and b) a herbicidally active amount of at least one cyclohexenone oxime ether of the formula I as defined in claim 1 during or after the sowing of the crop plants and before or during the emergence of the crop plants.

10. A method as defined in claim 9, wherein the crop plant is rice, wheat, corn, barley or millet.

11. A method for selectively controlling undesirable plant growth, which comprises simultaneously or successively treating the leaves of the crop plants and the undesirable plants postemergence with a) an antagonistically active amount of 3-(2-chlorophenylmethyl)-1-(1-methyl-1-phenylethyl)urea and/or 1-(1-methyl-1-phenylethyl)-3-(4-tolyl)urea and b) a herbicidally active amount of at least one cyclohexenone oxime ether of the formula I as defined in claim 1.

12. A method as defined in claim 11, wherein the crop plant is rice, wheat, corn, barley or millet.

13. The method of claim 11, wherein b is tralkoxydim.

14. A method of preventing damage to crop plants by herbicidal cyclohexenone oxime ethers of the formula I as defined in claim 1, which comprises treating the seed of the crop plants with an antagonistically active amount of 3-(2-chlorophenylmethyl-1-(1-methyl-1-phenylethyl)urea and/or 1-(1-methyl-1-phenylethyl)-3-(4-tolyl)urea.

15. A method as defined in claim 14, wherein the crop plant is rice, wheat, corn, barley or millet.

16. The method of claim 14, wherein the cyclohexenone oxime ether of the formula I is tralkoxydim.

* * * * *

UNITED STATES PATENT AND TRADEMARK OFFICE
CERTIFICATE OF CORRECTION

PATENT NO.: 5,605,875

DATED: February 25, 1997

INVENTOR(S): BRATZ et al.

It is certified that error appears in the above-identified patent and that said Letters Patent is hereby corrected as shown below:

In the title, item [54], "HERBICIDAL COMPOSITIONS COMPRISING 3-(2-CHLOROPHENYLMETHYL)-1-(1-METHYL-1-PHENYLETHYL)-AND/OR 1-(METHYL-1-PHENYLETHYL)-3-(4-TOLYL)UREA AND AT LEAST ONE CYCLOHEXENONE OXIME ETHER" should read: --HERBICIDAL COMPOSITIONS COMPRISING 3-(2-CHLOROPHENYLMETHYL)-1-(1-METHYL-1-PHENYLETHYL)-AND/OR 1-(1-METHYL-1-PHENYLETHYL)-3-(4-TOLYL)UREA AND AT LEAST ONE CYCLOHEXENONE OXIME ETHER--.

Column 10, claim 1, line 49, delete "hydrogen", second occurrence.

Column 10, claim 1, line 49 bridging line 50, "$C_2$-$C_6$-alkyl, also $C_2$-$C_6$-alkyl;" should read --$C_1$-$C_6$-alkyl, also $C_1$-$C_6$-alkyl;--.

Column 11, claim 2, line 48, "$C_1$-$C_6$alkyl" should read --$C_1$-$C_6$-alkyl--.

Column 12, claim 2, line 15, "$C_1$-$C_4$-alkoxY" should read --$C_1$-$C_4$-alkoxy Signed and Sealed this Twentieth Day of May, 1997

Attest:

BRUCE LEHMAN

Attesting Officer

Commissioner of Patents and Trademarks